(12) United States Patent
Park et al.

(10) Patent No.: US 11,854,142 B2
(45) Date of Patent: Dec. 26, 2023

(54) COMPUTING DEVICE FOR ALGORITHM TO RECONSTRUCT THREE-DIMENSIONAL TOMOGRAM BY CONSIDERING MULTIPLE SCATTERING, AND METHOD OF THE SAME

(71) Applicant: Korea Advanced Institute of Science and Technology, Daejeon (KR)

(72) Inventors: YongKeun Park, Daejeon (KR); Moosung Lee, Daejeon (KR); Herve Jerome Hugonnet, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 106 days.

(21) Appl. No.: 17/675,370

(22) Filed: Feb. 18, 2022

(65) Prior Publication Data

US 2023/0059661 A1 Feb. 23, 2023

(30) Foreign Application Priority Data

Aug. 23, 2021 (KR) .......................... 10-2021-0111115

(51) Int. Cl.
*G06T 15/20* (2011.01)
*G16H 30/40* (2018.01)

(52) U.S. Cl.
CPC .......... *G06T 15/205* (2013.01); *G16H 30/40* (2018.01); *G06T 2200/08* (2013.01); *G06T 2207/10081* (2013.01)

(58) Field of Classification Search
None
See application file for complete search history.

(56) References Cited

U.S. PATENT DOCUMENTS

2020/0378745 A1* 12/2020 Li ....................... G01B 9/02091
2022/0155440 A1* 5/2022 Kruse ...................... A61B 8/54

FOREIGN PATENT DOCUMENTS

WO WO 2017-213464 12/2017
WO WO-2017213464 A1 * 12/2017 ............... G01B 9/02

OTHER PUBLICATIONS

Harada, Haruyuki, et al. "Conjugate gradient method applied to inverse scattering problem." IEEE Transactions on Antennas and Propagation 43.8 (1995): 784-792. (Year: 1999).*
Trattner, Sigal, et al. "Can Born approximate the unborn? A new validity criterion for the Born approximation in microscopic imaging. "2007 IEEE 11th International Conference on Computer Vision. IEEE, 2007. (Year: 2007).*

(Continued)

*Primary Examiner* — Nurun Flora
(74) *Attorney, Agent, or Firm* — Christensen O'Connor Johnson Kindness PLLC

(57) ABSTRACT

Various example embodiments provide a computing device of an algorithm for reconstructing a three-dimensional (3D) image in consideration of multiple scattering and a method of the same. According to various example embodiments, the computing device may be configured to set a 3D refractive index based on a plurality of 2D images for a specimen and to reconstruct a 3D image for the specimen from the set refractive index using a modified Born expansion considering multiple scattering to converge a calculation result.

20 Claims, 8 Drawing Sheets

(56) References Cited

OTHER PUBLICATIONS

Osnabrugge, Gerwin, Saroch Leedumrongwatthanakun, and Ivo M. Vellekoop. "A convergent Born series for solving the inhomogeneous Helmholtz equation in arbitrarily large media." Journal of computational physics 322 (2016): 113-124. (Year: 2016).*

Geon K reference translation is provided (Year: 2017).*

International Search Report for PCT/KR2022/002458 (filed Feb. 18, 2022), dated May 27, 2022.

R.E. Kleinman, Convergent Born series for large refractive indices, Journal of the Optical Society of America A, vol. 7, Issue 5, pp. 890-897, May 1, 1990 (2022), <https://opg.optica.org/josaa/abstract.cfm?uri=josaa-7-5-890>.

Moosung Lee, Inverse problem solver for multiple light scattering using modified Born series, Optica, vol. 9, Issue 2, pp. 177-182, Feb. 2, 2022 (2022) <https://opg.optica.org/optica/fulltext.cfm?uri=optica-9-2-177&id=469071>.

Korean Office Action for KR 10-2021-0111115, dated May 10, 2023.

Gerwin Osnabrugge, A convergent Born series for solving the inhomogeneous Helmholtz equation in arbitrarily large media, Journal of Computational Physics, vol. 322, pp. 113-124, Jun. 27, 2016 (2022) <https://www.sciencedirect.com/science/article/pii/S0021999116302595>.

Michael Chen, Multi-layer Born multiple-scattering model for 3D phase microscopy, Optica, vol. 7, Issue 5, pp. 394-403, Apr. 28, 2020 (2022) <https://opg.optica.org/optica/fulltext.cfm?uri=optica-7-5-394&id=431219>.

* cited by examiner

COMPUTING DEVICE FOR ALGORITHM TO RECONSTRUCT THREE-DIMENSIONAL TOMOGRAM BY CONSIDERING MULTIPLE SCATTERING, AND METHOD OF THE SAME

TECHNICAL FIELD

Various example embodiments of the following description relate to a computing device of an algorithm for reconstructing a three-dimensional (3D) image in consideration of multiple scattering and a method of the same.

BACKGROUND OF THE DISCLOSURE

A method of constructing a single three-dimensional (3D) image from a plurality of two-dimensional (2D) images is used in various fields. X-ray computed tomography (CT) is used in the medical imaging field and 3D quantitative phase imaging (QPI) or optical diffraction tomography (ODT) that measures a 3D refractive index through holographic measurement is used in the biological field. Currently, atomic electron tomography that performs reconstruction based on 2D electron microscopy images is used to study basic physical properties.

A tomographic imaging construction methodology follows a method of constructing 3D physical property information of a target to be measured by reversely solving a wave equation using information about a plurality of 2D images basically measured. Here, it is a problem that a method of efficiently finding an exact solution of an equation in a reverse manner is unknown since the wave equation is an equation in a second-order differential form. To solve this problem, a method of linearizing a wave equation through a weak scattering assumption has been adopted for a long time. The linearized wave equation is easily solved in a reverse manner and thus, has been used in various fields. However, in the case of a specimen in a complex internal structure or an external environment with severe scattering, it may be impossible to reconstruct an accurate 3D image. Alternatively, although the 3D image is reconstructed, a shape or a value may be severely distorted.

To alleviate a distortion issue of a result value caused by not considering multiple scattering, regularization methodology has been mainly used, which is a method of modifying reconstructed 3D image information based on prior information or assumption about a specimen. Algorithms, such as a non-negativity regularization that a refractive index of a specimen is higher than that of a background of the specimen, a total variation minimization, a theory of super-resolution in resonant media, and a deep learning algorithm, are applied.

However, the methods depend on various assumptions and conditions and do not fundamentally solve a multi-scattering issue. As a representative method for solving multiple scattering, there is a finite-difference time-domain (FDTD) method. However, a large amount of computational time is required. To outperform this, proposed are a multi-layer Born approximation, a beam propagation method, and the like. However, since the methods refer to an approximation method in terms of arithmetic theory, they provide inaccurate reconstruction results.

SUMMARY

Various example embodiments provide a computing device for reconstructing an accurate and distortion-free three-dimensional (3D) image in consideration of multiple scattering and a method of the same.

Various example embodiments provide a computing device of an algorithm for reconstructing a 3D image in consideration of multiple scattering and a method of the same.

According to various example embodiments, a method of a computing device may include setting a 3D refractive index based on a plurality of two-dimensional (2D) images for a specimen; and reconstructing a 3D image for the specimen from the set refractive index using a modified Born expansion considering multiple scattering to converge a calculation result.

According to various example embodiments, the computing device may include an image measurer configured to measure a plurality of 2D images for a specimen; and an image reconstructor configured to set a 3D refractive index based on the 2D images and to reconstruct a 3D image for the specimen from the set refractive index using a modified Born expansion considering multiple scattering to converge a calculation result.

According to various example embodiments, a computing device may accurately and quickly reconstruct a 3D image even in a multi-scattering environment. That is, the computing device may implement a 3D tomography reconstruction in a general light scattering condition, such as a weak scattering, without any assumption by applying a modified Born expansion to a 3D image construction algorithm. The computing device may provide a calculation speed that is 100 times or more faster with the same accuracy than a calculation method according to an existing finite-difference time-domain (FDTD) method.

DETAILED DESCRIPTION

Hereinafter, various example embodiments disclosed herein will be described with reference to the accompanying drawings.

The present disclosure proposes an algorithm that considers multiple scattering when reconstructing a three-dimensional (3D) stereoscopic image constituting a single 3D image from a plurality of two-dimensional (2D) images. The present disclosure provides methodology that may construct a stereoscopic image without assumption even in a specimen with severe scattering. The keypoint of the present disclosure lies in employing a method of directly substituting measured 2D image information into a wave equation using a modified Born expansion (modified Born series) method. Through this, the present disclosure enables an accurate and fast 3D image reconstruction even in a multi-scattering environment.

The present disclosure implements a 3D tomography reconstruction in a general light scattering condition, such as a weak scattering, without any assumption by applying a modified Born expansion to a 3D image construction algorithm. The present disclosure provides a calculation speed that is 100 times or more faster with the same accuracy than a calculation method according to an existing finite-difference time-domain (FDTD) method.

Figure 1:
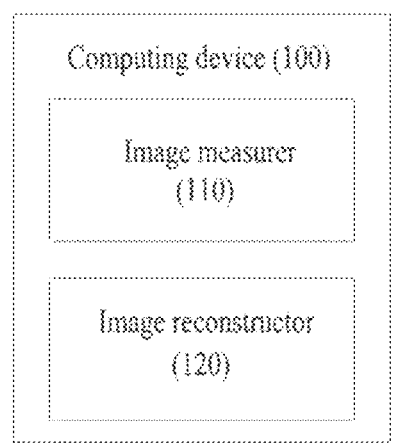
FIG. 1 is a diagram illustrating a computing device according to various example embodiments.
Figure 2:
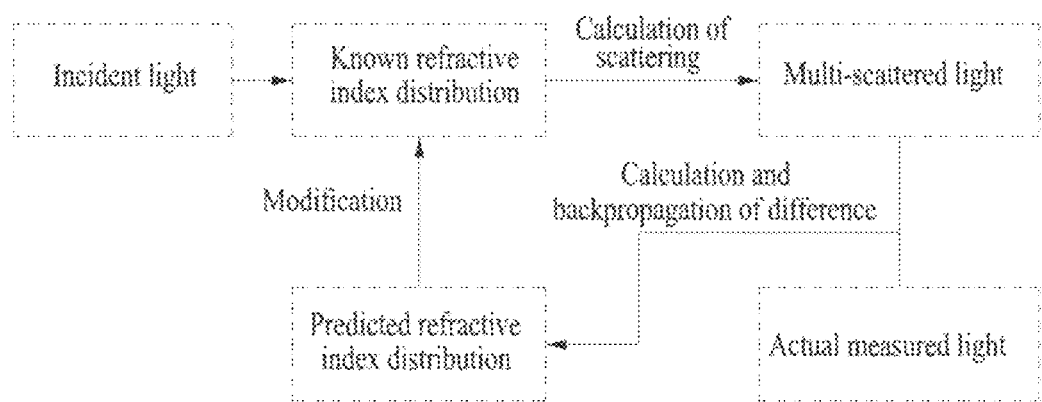
FIG. 2 illustrates an operation characteristic of a computing device according to various example embodiments.

FIG. 1 is a diagram illustrating a computing device 100 according to various example embodiments. FIG. 2 illustrates an operation characteristic of the computing device 100 according to various example embodiments.

Referring to FIG. 1, the computing device 100 may include an image measurer 110 and an image reconstructor 120.

The image measurer 110 may measure a plurality of 2D images for a specimen. That is, referring to FIG. 2, the image measurer 110 may measure 2D images from an incident light that passes through a specimen. According to an example embodiment, although not illustrated, the image measurer 110 may include a light source system, an optical system, and a camera. Here, the specimen may be provided between the light source system and the optical system. The light source system may irradiate light toward the specimen, and the optical system may provide the light that passes through the specimen to the camera. Through this, the camera may actually measure 2D images of the specimen. To this end, the camera may include at least one image sensor. Alternatively or additionally, at least one another component may be added to the image measurer 110.

The image reconstructor 120 may reconstruct a 3D image by applying a 3D image reconstruction algorithm considering multiple scattering based on the plurality of 2D images measured by the image measurer 110. In detail, referring to FIG. 2, the image reconstructor 120 may detect a known refractive index distribution based on the incident light through a weak scattering assumption. Here, the image reconstructor 120 may construct a single 3D image based on the plurality of 2D images measured by the image measurer 110 through Born approximation or Rytov approximation and the constructed 3D image may be detected using the known refractive index distribution. As illustrated in FIG. 2, the image reconstructor 120 may calculate a scattering based on the known refractive index distribution and may detect a multi-scattered light. Also, as illustrated in FIG. 2, the image reconstructor 120 may calculate a difference between the multi-scattered light and an actual measured light and may backpropagate the difference. Here, the image reconstructor 120 may backpropagate the difference in a direction of the specimen using a modified Born expansion. Here, the modified Born expansion is described below with reference to FIGS. 3 and 4. Through this, as illustrated in FIG. 2, the image reconstructor 120 may reconstruct the 3D image based on a 3D pattern of the backpropagated light. Here, the image reconstructor 120 may detect a predicted refractive index distribution from the 3D image and may modify the known refractive index distribution using the predicted refractive index distribution. In this manner, the image reconstructor 120 may repeatedly reconstruct the 3D image until the 3D image converges.

According to various example embodiments, the computing device 100 may provide an excellent reconstruction accuracy compared to an existing reconstruction method assuming that a light scattering is weak. That is, the computing device 110 may provide a calculation speed that is 100 times or more faster with the same accuracy than a calculation method according to an existing FDTD method.

Figure 3:
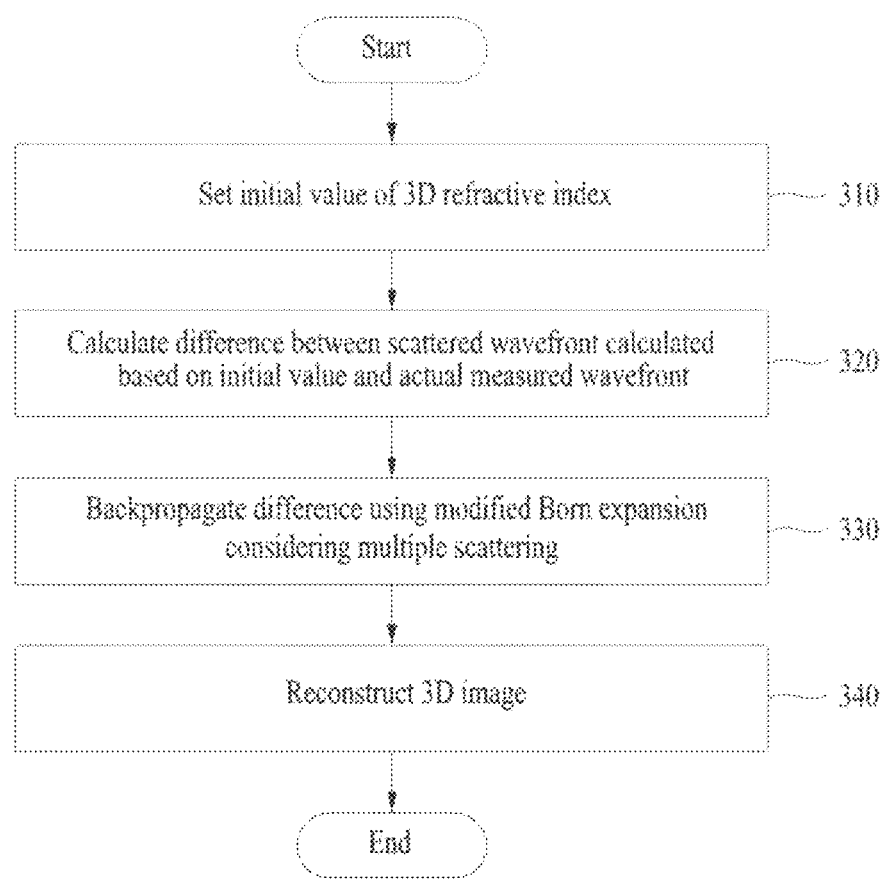
FIG. 3 is a flowchart illustrating a method of a computing device according to various example embodiments.
Figure 4:
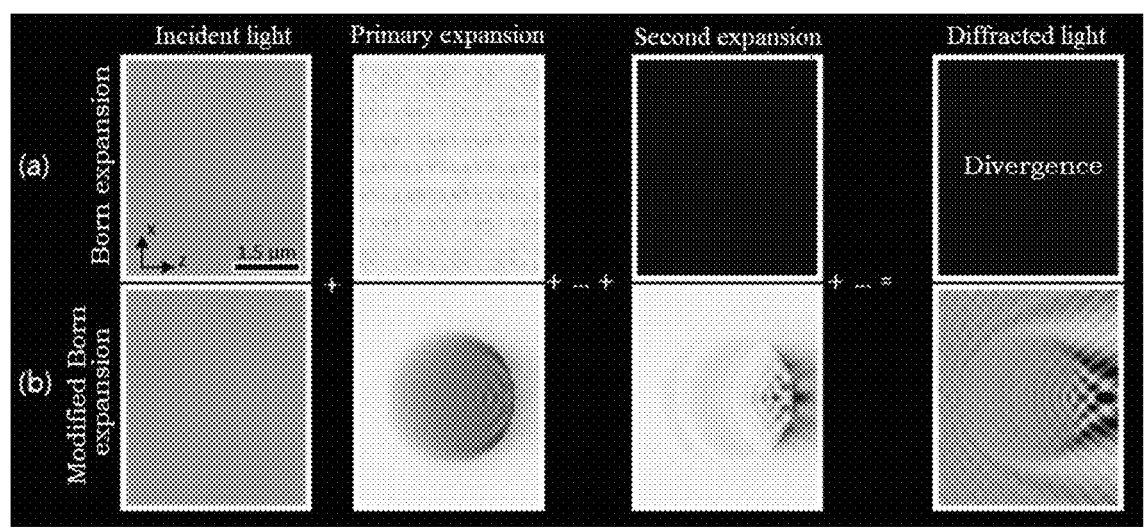
FIGS. 4 and 5 illustrate an example of a method of a computing device according to various example embodiments.
Figure 5:
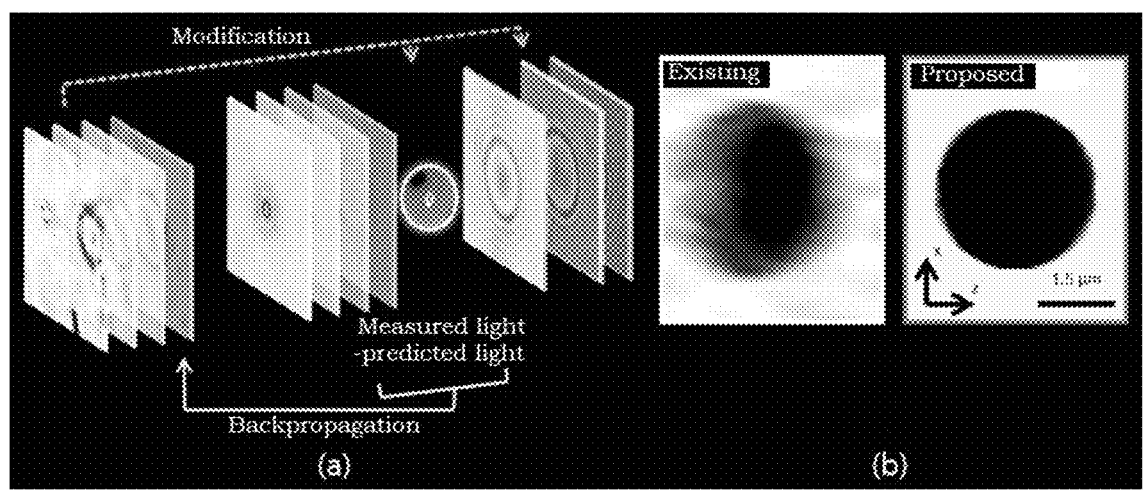

FIG. 3 is a flowchart illustrating a method of the computing device 100 according to various example embodiments. FIGS. 4 and 5 illustrate an example of a method of the computing device 100 according to various example embodiments.

Referring to FIG. 3, in operation 310, the computing device 100 may set an initial value of a 3D refractive index. Here, the computing device 100 may set the initial value of the 3D refractive index through weak scattering assumption. In detail, the image reconstructor 120 may construct a single 3D image based on a plurality of 2D images measured by the image measurer 110 through Born approximation and Rytov approximation. The constructed 3D image may be set as the initial value of the 3D refractive index.

In operation 320, the computing device 100 may calculate a difference between a scattered wavefront calculated based on the initial value and an actual measured wavefront. In detail, the image reconstructor 120 may calculate a scattered wavefront to an image sensor position of the image measurer 110 based on the initial value. The image reconstructor 120 may calculate the difference between the calculated wavefront and the actual measured wavefront.

In operation 330, the computing device 100 may backpropagate the difference using a modified Born expansion (modified Born series) considering multiple scattering. That is, the image reconstructor 120 may backpropagate the difference in a direction of the specimen using the modified Born expansion. In general, to solve a light scattering, a solution of Lippman-Schwinger equation needs to be found. In this process, an inverse matrix of a matrix with a size of 1,000,000×1,000,000 or more needs to be calculated. To effectively calculate this, as illustrated in (a) of FIG. 4, although a Born expansion using a Taylor expansion (Taylor series) for the inverse matrix is illustrated, this expansion has a problem of divergence. Therefore, the present disclosure may modify the existing Born expansion and may implement the modified Born expansion in which a calculation result may converge at all times as illustrated in (b) of FIG. 4. To this end, dissimilar to the Born expansion used in the art, the modified Born expansion may be designed such that a background medium may absorb light. Here, according to Huygens' principle, the light may be scattered and propagated as an evanescent wave instead of a spherical wave. In the case of mathematically describing scattering as the evanescent wave, the convergence radius of the Taylor expansion increases in proportion to absorbance of the background medium. Therefore, since the absorbance of the background medium may be arbitrarily adjusted in a simulation, the calculation result may be implemented to converge through the modified Born expansion.

In operation 340, the computing device 100 may reconstruct the 3D image. Here, the image reconstructor 120 may modify the 3D image constructed in operation 210 based on a 3D pattern of the propagated light. Through this, as illustrated in (a) of FIG. 5, the image reconstructor 120 may construct a tomography image of actual measured light from a tomography image of predicted light. Here, to compensate for insufficient information about the specimen in a modification process, a proximal gradient descent scheme may be applied.

In some example embodiments, the computing device 100 may repeat operations 310 to 340. That is, the computing device 100 may repeat operations 310 to 340 until the reconstructed 3D image converges. In detail, the image reconstructor 120 may determine whether the reconstructed 3D image converges in operation 340. Here, unless the reconstructed 3D image converges, the image reconstructor 120 may return to operation 310 and may update the set initial value of the 3D refractive index based on the reconstructed 3D image. Next, the image reconstructor 120 may repeat operations 320 to 340. Meanwhile, when the reconstructed 3D image converges in operation 340, the image reconstructor 120 may determine the finally reconstructed 3D image as a final tomography image.

According to various example embodiments, the computing device 100 may provide more excellent reconstruction accuracy than the existing reconstruction method assuming that a light scattering is weak, as illustrated in (b) of FIG. 5. That is, the computing device 110 may provide a calculation speed that is 100 times or more faster with the same accuracy than a calculation method according to an existing FDTD method.

Figure 6A:
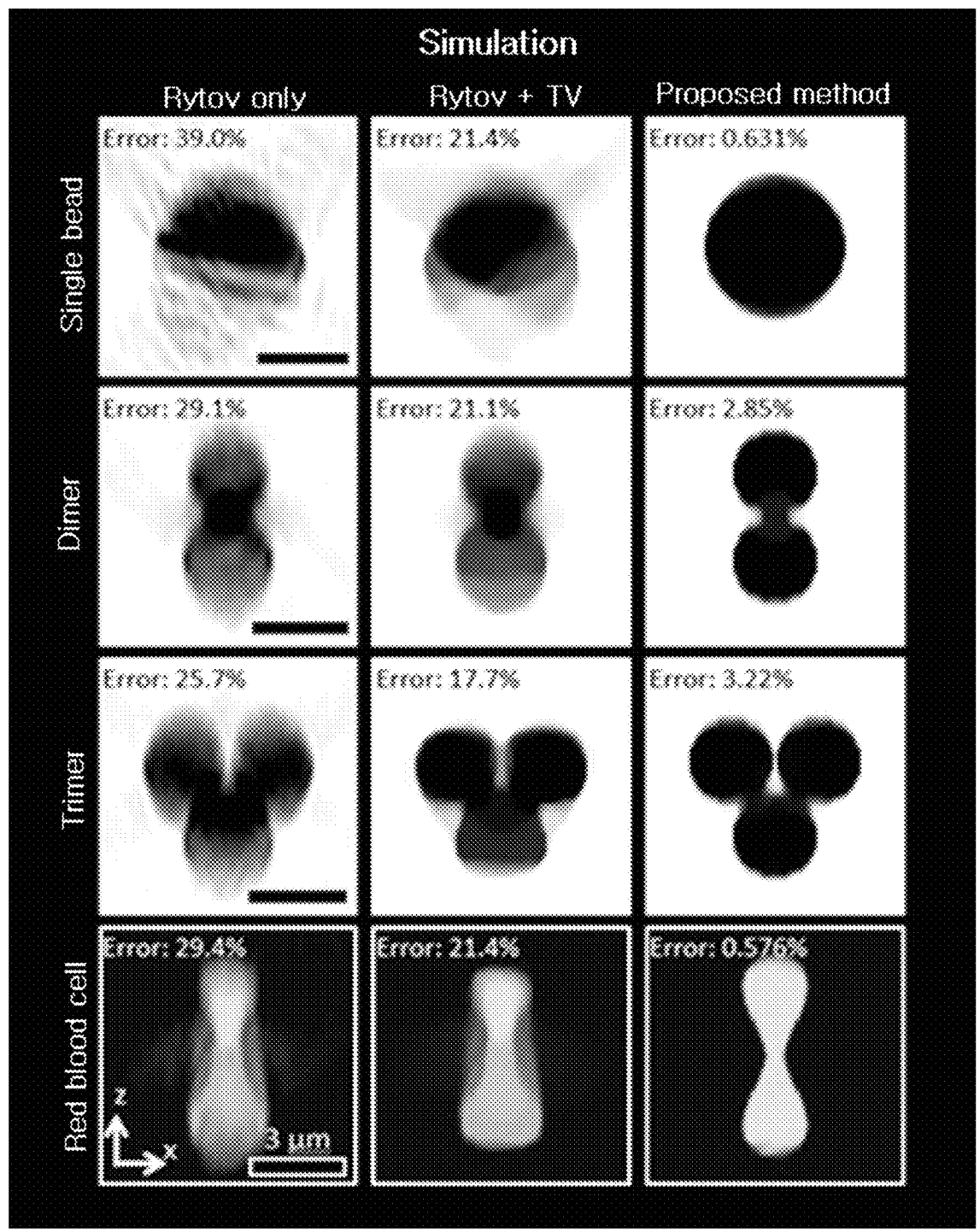
FIGS. 6A, 6B, and 6C illustrate verification results about an operation characteristic of a computing device according to various example embodiments.
Figure 6B:
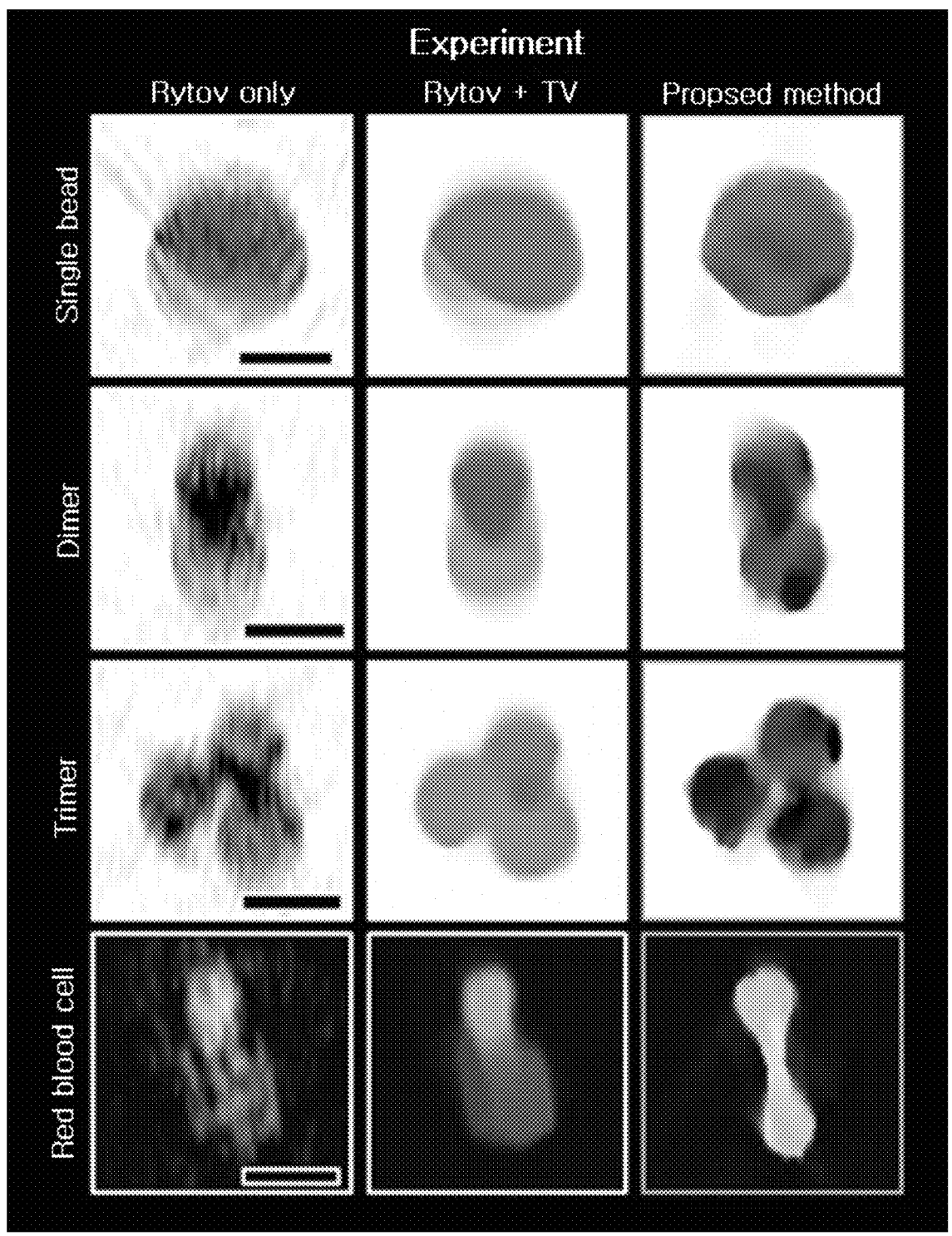
Figure 6C:
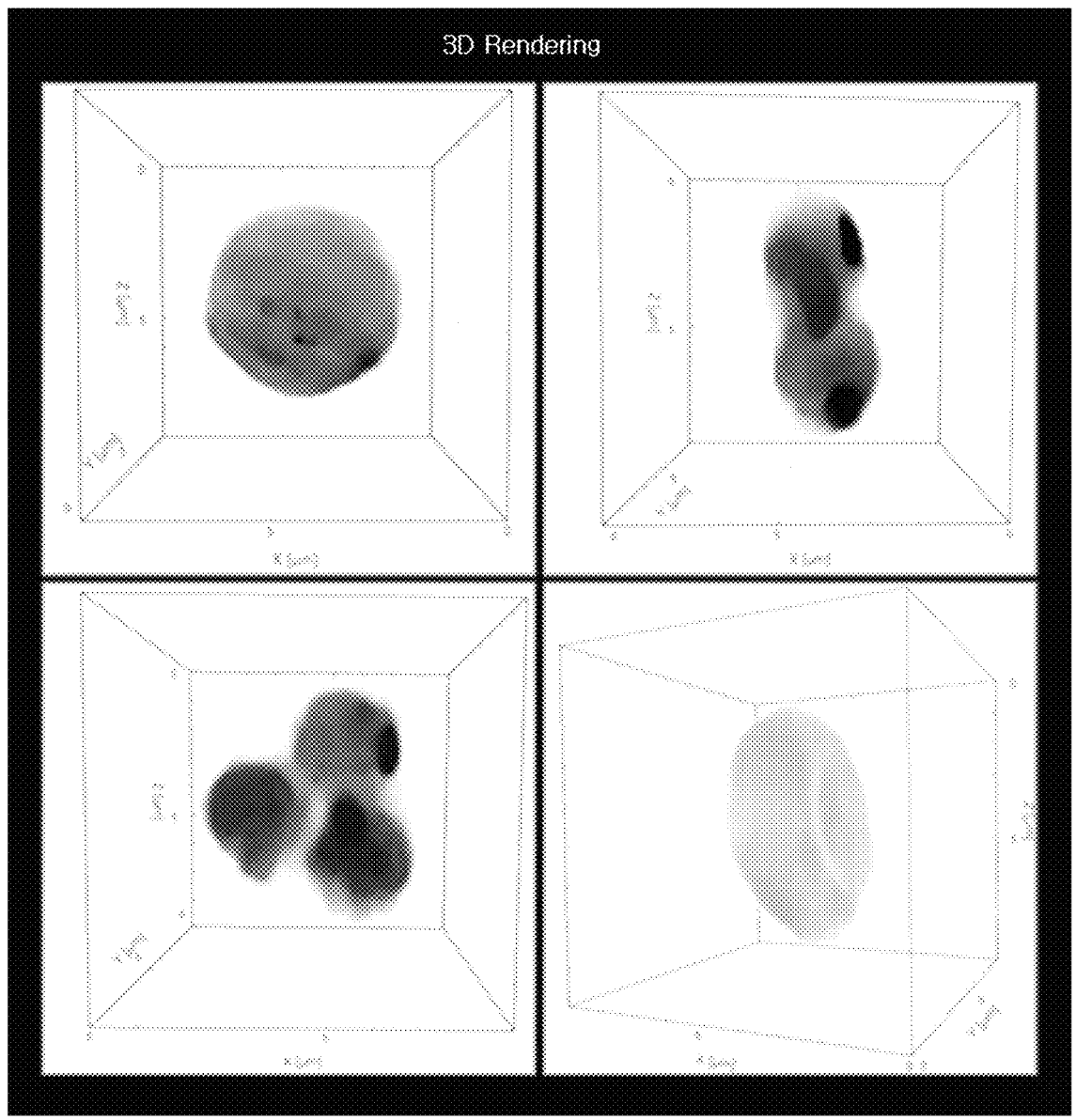

FIGS. 6A, 6B, and 6C illustrate verification results about an operation characteristic of the computing device 100 according to various example embodiments. FIG. 6A illustrates a numerical simulation result, FIG. 6B illustrates an experimental verification result, and FIG. 6C illustrates a 3D rendering result of FIG. 6B.

Referring to FIGS. 6A, 6B, and 6C, a numerical simulation and an experimental verification for a 3D image reconstruction algorithm according to various example embodiments were performed. FIGS. 6A, 6B, and 6C show results of applying an image reconstruction algorithm according to various example embodiments to a specimen in which multiple scattering occurs, such as single plastic particle (single bead), dimer, trimer, red blood cell, and the like.

A stereoscopic image construction was distorted and a result value was changed in a result by applying Rytov approximation to the existing optical diffraction tomography (ODT). This is due to multiple scattering that occurs when a difference between a refractive index of the specimen and a refractive index of a medium is great. In the case of applying a TV normalization methodology, a difference in distortion may be attenuated, but a shape or a value of the actual specimen is not accurately reflected. However, in the case of applying the 3D image reconstruction algorithm according to various example embodiments, not only the entire stereoscopic image but also the result value of the refractive index may be accurately extracted.

Therefore, the present disclosure enables restoration of an accurate and distortion-free result value in consideration of multiple scattering in the field of 3D stereoscopic image measurement. The scope of application of the present disclosure may be applicable to all techniques for constructing a single 3D stereoscopic image from a plurality of 2D images by reversely solving a wave equation. The present disclosure may broadly apply to the technical field including, for example, X-ray computed tomography (CT), optical coherence tomography, and atomic electron tomography.

A method of the computing device 100 according to various example embodiments may include operation 310 of setting a 3D refractive index based on a plurality of 2D images for a specimen, and operations 320, 330, and 340 of reconstructing a 3D image for the specimen from the set refractive index using a modified Born expansion considering multiple scattering to converge a calculation result.

According to various example embodiments, operations 320, 330, and 340 of reconstructing the 3D image may include operation 320 of calculating a difference between a scattered wavefront calculated based on the set refractive index and an actual measured wavefront, operation 330 of backpropagating the difference using the modified Born expansion, and operation 340 of reconstructing the 3D image by modifying the set refractive index based on a 3D pattern for the backpropagated difference.

According to various example embodiments, operation 310 of setting the 3D refractive index may include constructing a 3D image based on the 2D images through predetermined scattering assumption, and setting the constructed 3D image as the 3D refractive index.

According to various example embodiments, operation 320 of calculating the difference may include calculating a scattered wavefront to an image sensor position at which the 2D images are measured, based on the 3D refractive index, and calculating the difference between the scattered wavefront and the actual measured wavefront.

According to various example embodiments, operation 340 of reconstructing the 3D image by modifying the set refractive index may comprise modifying the set refractive index by applying a proximal gradient descent scheme.

According to various example embodiments, operations 320, 330, and 340 of reconstructing the 3D image may be repeated until the reconstructed 3D image converges.

According to various example embodiments, operations 320, 330, and 340 of reconstructing the 3D image may include updating the set refractive index based on the reconstructed 3D image unless the reconstructed 3D image converges.

According to various example embodiments, the method of the computing device 100 may further include determining the reconstructed 3D image as a final tomography image when the reconstructed 3D image converges.

The computing device 100 according to various example embodiments may include the image measurer 110 configured to measure a plurality of 2D images for a specimen, and the image reconstructor 120 configured to set a 3D refractive index based on the 2D images and to reconstruct a 3D image for the specimen from the set refractive index using a modified Born expansion considering multiple scattering to converge a calculation result.

According to various example embodiments, the image reconstructor 120 may be configured to calculate a difference between a scattered wavefront calculated based on the set refractive index and an actual measured wavefront, to backpropagate the difference using the modified Born expansion, and to reconstruct the 3D image by modifying the set refractive index based on a 3D pattern for the backpropagated difference.

According to various example embodiments, the image reconstructor 120 may be configured to construct a 3D image based on the 2D images through predetermined scattering assumption, and to set the constructed 3D image as the 3D refractive index.

According to various example embodiments, the image reconstructor 120 may be configured to calculate a scattered wavefront to an image sensor position at which the 2D images are measured, based on the 3D refractive index, and to calculate the difference between the scattered wavefront and the actual measured wavefront.

According to various example embodiments, the image reconstructor 120 may be configured to modify the set refractive index by applying a proximal gradient descent scheme.

According to various example embodiments, the image reconstructor 120 may be configured to repeatedly reconstruct the 3D image until the converging 3D image is reconstructed.

According to various example embodiments, the image reconstructor 120 may be configured to update the set refractive index based on the reconstructed 3D image unless the reconstructed 3D image converges.

According to various example embodiments, the image reconstructor 120 may be configured to determine the reconstructed 3D image as a final tomography image when the reconstructed 3D image converges.

The apparatuses described herein may be implemented using hardware components, software components, and/or a combination of hardware components and software components. For example, a processing device and components described herein may be implemented using one or more general-purpose or special purpose computers, for example, a processor, a controller, an arithmetic logic unit (ALU), a digital signal processor, a microcomputer, a field programmable gate array (FPGA), a programmable logic unit (PLU), a microprocessor, or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will be appreciated that a processing device may include multiple processing elements and/or multiple types of processing elements. For example, a processing device may include multiple processors or a processor and a controller. In addition, other processing configurations are possible, such as parallel processors.

The software may include a computer program, a piece of code, an instruction, or some combination thereof, for independently or collectively instructing or configuring the processing device to operate as desired. Software and/or data may be embodied in any type of machine, component, physical equipment, computer storage medium or device, to provide instructions or data to the processing device or be interpreted by the processing device. The software also may be distributed over network coupled computer systems so that the software is stored and executed in a distributed fashion. The software and data may be stored by one or more computer readable storage mediums.

The methods according to various example embodiments may be implemented in a form of a program instruction executable through various computer methods and recorded in computer-readable media. Here, the media may be to continuously store a computer-executable program or to temporarily store the same for execution or download. The media may be various types of record methods or storage methods in which single hardware or a plurality of hardware is combined and may be distributed over a network without being limited to a medium that is directly connected to a computer system. Examples of the media include magnetic media such as hard disks, floppy disks, and magnetic tapes; optical media such as CD ROM and DVD; magneto-optical media such as floptical disks; and hardware devices that are specially configured to store and perform program instructions, such as read-only memory (ROM), random access memory (RAM), flash memory, and the like. Examples of other media may include recording media and storage media managed by an app store that distributes applications or a site, a server, and the like that supplies and distributes other various types of software.

Various example embodiments and the terms used herein are not construed to limit description disclosed herein to a specific implementation and should be understood to include various modifications, equivalents, and/or substitutions of a corresponding example embodiment. In the drawings, like reference numerals refer to like components throughout the present specification. The singular forms "a," "an," and "the" are intended to include the plural forms as well, unless the context clearly indicates otherwise. Herein, the expressions, "A or B," "at least one of A and/or B," "A, B, or C," "at least one of A, B, and/or C," and the like may include any possible combinations of listed items. Terms "first," "second," etc., are used to describe corresponding components regardless of order or importance and the terms are simply used to distinguish one component from another component. The components should not be limited by the terms. When a component (e.g., a first component) is described to be "(functionally or communicatively) connected to" or "accessed to" another component (e.g., a second component), the component may be directly connected to the other component or may be connected through still another component (e.g., a third component).

The term "module" used herein may include a unit configured as hardware, software, or firmware, and may be interchangeably used with the terms, for example, "logic," "logic block," "part," "circuit," etc. The module may be an integrally configured part, a minimum unit that performs at least function, or a portion thereof. For example, the module may be configured as an application-specific integrated circuit (ASIC).

According to various example embodiments, each of the components (e.g., module or program) may include a singular object or a plurality of objects. According to various example embodiments, at least one of the components or operations may be omitted. Alternatively, at least one another component or operation may be added. Alternatively or additionally, a plurality of components (e.g., module or program) may be integrated into a single component. In this case, the integrated component may perform one or more functions of each of the components in the same or similar manner as it is performed by a corresponding component before integration. According to various example embodiments, operations performed by a module, a program, or another component may be performed in a sequential, parallel, iterative, or heuristic manner. Alternatively, at least one of the operations may be performed in different sequence or omitted. Alternatively, at least one another operation may be added.

The invention claimed is:

1. A method of a computing device, the method comprising:
   setting a three-dimensional (3D) refractive index based on a plurality of two-dimensional (2D) images for a specimen; and
   reconstructing a 3D image for the specimen from the set refractive index using a modified Born expansion considering multiple scattering to converge a calculation result.

2. The method of claim 1, wherein the reconstructing of the 3D image comprises:
   calculating a difference between a scattered wavefront calculated based on the set refractive index and an actual measured wavefront;
   backpropagating the difference using the modified Born expansion; and
   reconstructing the 3D image by modifying the set refractive index based on a 3D pattern for the backpropagated difference.

3. The method of claim 1, wherein the setting of the 3D refractive index comprises:
   constructing a 3D image based on the 2D images through predetermined scattering assumption; and setting the constructed 3D image as the 3D refractive index.

4. The method of claim 2, wherein the calculating of the difference comprises:
   calculating a scattered wavefront to an image sensor position at which the 2D images are measured, based on the 3D refractive index; and
   calculating the difference between the scattered wavefront and the actual measured wavefront.

5. The method of claim 2, wherein the reconstructing of the 3D image by modifying the set refractive index comprises modifying the set refractive index by applying a proximal gradient descent scheme.

6. The method of claim 1, wherein the reconstructing of the 3D image is repeated until the reconstructed 3D image converges.

7. The method of claim 6, wherein the reconstructing of the 3D image comprises updating the set refractive index based on the reconstructed 3D image unless the reconstructed 3D image converges.

8. The method of claim 1, further comprising:
   determining the reconstructed 3D image as a final tomography image when the reconstructed 3D image converges.

9. A computing device comprising:
   an image measurer configured to measure a plurality of two-dimensional (2D) images for a specimen; and
   an image reconstructor configured to set a three-dimensional (3D) refractive index based on the 2D images and to reconstruct a 3D image for the specimen from the set refractive index using a modified Born expansion considering multiple scattering to converge a calculation result.

10. The computing device of claim 9, wherein the image reconstructor is configured to,
    calculate a difference between a scattered wavefront calculated based on the set refractive index and an actual measured wavefront,
    backpropagate the difference using the modified Born expansion, and
    reconstruct the 3D image by modifying the set refractive index based on a 3D pattern for the backpropagated difference.

11. The computing device of claim 9, wherein the image reconstructor is configured to,
    construct a 3D image based on the 2D images through predetermined scattering assumption, and
    set the constructed 3D image as the 3D refractive index.

12. The computing device of claim 10, wherein the image reconstructor is configured to,
    calculate a scattered wavefront to an image sensor position at which the 2D images are measured, based on the 3D refractive index, and
    calculate the difference between the scattered wavefront and the actual measured wavefront.

13. The computing device of claim 10, wherein the image reconstructor is configured to modify the set refractive index by applying a proximal gradient descent scheme.

14. The computing device of claim 9, wherein the image reconstructor is configured to repeatedly reconstruct the 3D image until the converging 3D image is reconstructed.

15. The computing device of claim 14, wherein the image reconstructor is configured to update the set refractive index based on the reconstructed 3D image unless the reconstructed 3D image converges.

16. The computing device of claim 9, wherein the image reconstructor is configured to determine the reconstructed 3D image as a final tomography image when the reconstructed 3D image converges.

17. A non-transitory computer-readable storage medium storing one or more programs to implement a method in a computing device, wherein the method comprises:
    setting a three-dimensional (3D) refractive index based on a plurality of two-dimensional (2D) images for a specimen; and
    reconstructing a 3D image for the specimen from the set refractive index using a modified Born expansion considering multiple scattering to converge a calculation result.

18. The non-transitory computer-readable storage medium of claim 17, wherein the reconstructing of the 3D image comprises:
    calculating a difference between a scattered wavefront calculated based on the set refractive index and an actual measured wavefront;
    backpropagating the difference using the modified Born expansion; and
    reconstructing the 3D image by modifying the set refractive index based on a 3D pattern for the backpropagated difference.

19. The non-transitory computer-readable storage medium of claim 17, wherein the setting of the 3D refractive index comprises:
    constructing a 3D image based on the 2D images through predetermined scattering assumption; and
    setting the constructed 3D image as the 3D refractive index.

20. The non-transitory computer-readable storage medium of claim 17, wherein the reconstructing of the 3D image is repeated until the reconstructed 3D image converges.

* * * * *